(12) United States Patent
Singh et al.

(10) Patent No.: US 6,582,971 B1
(45) Date of Patent: Jun. 24, 2003

(54) IMPRINTING LARGE MOLECULAR WEIGHT COMPOUNDS IN POLYMER COMPOSITES

(75) Inventors: Waheguru Pal Singh; Anthony Giletto; David Gaskin, all of College Station; James Fyffe, Bryan, all of TX (US)

(73) Assignee: Lynntech, Inc., College Station, TX (US)

( * ) Notice: Subject to any disclaimer, the term of this patent is extended or adjusted under 35 U.S.C. 154(b) by 83 days.

(21) Appl. No.: 09/642,796

(22) Filed: Aug. 21, 2000

(51) Int. Cl.$^7$ ............................................. G01N 33/543
(52) U.S. Cl. ..................... 436/518; 436/524; 436/8; 436/85; 521/99; 521/100; 521/102; 501/80; 210/660
(58) Field of Search ........................... 435/7.1; 436/518, 436/85, 528, 529, 530, 531, 829, 524, 8; 526/201, 911; 428/357; 501/80; 521/99, 100

(56) References Cited

U.S. PATENT DOCUMENTS

| | | | |
|---|---|---|---|
| 5,110,833 A | | 5/1992 | Mosbach |
| 5,461,175 A | | 10/1995 | Fischer |
| 5,756,717 A | | 5/1998 | Paliwai |
| 5,814,223 A | | 9/1998 | Hjerten |
| 5,821,311 A | * | 10/1998 | Mosbach et al. ............ 526/201 |
| 6,127,154 A | * | 10/2000 | Mosbach et al. ......... 435/173.1 |
| 6,310,110 B1 | * | 10/2001 | Markowitz et al. ............ 521/99 |

OTHER PUBLICATIONS

The Emerging Technique of Molecular Imprinting and its Future Impact on Biotechnology, Biotechnology vol. 14, 1996, pp. 163–170.*

Highly selective separations by capillary electrochromatography: molecular imprint polymer sorbents, Journal of Chromatography A, 887 (2000) 125–135.*

Recent advances in the use of molecularly imprinted materials in separation and synthesis, American Chemical Society, Chapter 5, pp. 82–89. ACS Symposium Series.*

*Macromolecules* 1997, 30; "Metal Iron–Imprinted Polymer Prepared by the Combination of Surface Template Polymerization with Postirradiation by $y$–rays";pp. 3888–3891; Kazuya Uezu, Hiroki Nakamura, Jun–ichi Kanno, et al.

Chemtech April 1999; "Molecular recognition using surface template polymerization"; pp. 12–18; Kazuya Uezu, Masahiro Yoshida; Masahiro Goto; Shintaro Furusaki.

Journal of Chemical Engineering of Japan, vol. 32, No. 3, pp. 262–267:1999; Metal–Imprinted Mircosphere Prepared by Surface Template Polymerization with W/O/W Emulsions; Kazuyo Uezu, et al.

* cited by examiner

Primary Examiner—Long V. Le
Assistant Examiner—Gary W. Counts
(74) Attorney, Agent, or Firm—Streets & Steele; Jeffrey L. Streets (57) ABSTRACT

A method for molecular imprinting polymers with large biomolecules. The imprinted polymer composite is made by the interfacial polymerization of a monomer in the presence of the print molecule and host polymer. Since polymerization occurs at the interface between an organic solvent and an aqueous solution, the print molecule can be disposed in the phase that allows the print molecule to remain in its native configuration. The choice of the host polymer and the monomer to be polymerized can be varied to enhance the specificity of the composite toward the biomolecule that is selected to be imprinted.

97 Claims, 4 Drawing Sheets

IMPRINTING LARGE MOLECULAR WEIGHT COMPOUNDS IN POLYMER COMPOSITES

This invention was made with Government support under grant number 1 R43 GM61436-01 awarded by the National Institutes of Health (NIH). The Government has certain rights in this invention.

BACKGROUND OF THE INVENTION

1. Field of the Invention

This invention relates to molecularly imprinted polymer compositions, as well as methods of making and using the compositions. The invention further relates to methods of making and using molecularly imprinted polymer compositions for molecular recognition of various biomolecules, particularly high molecular weight biological macromolecules.

2. Background of the Related Art

Current biomolecular recognition elements for large proteins and other large molecular weight biological compounds rely on fragile biomolecules for recognition of the target analyte. The recognition elements typically include antibodies, nucleic acid probes, enzymes, and/or other receptors. These recognition elements are expensive to prepare, especially in large quantities, and are physically and chemically fragile. In addition, the utility of sensors and separation media that use these fragile recognition elements is limited because of their expense and fragility. A need exists for an inexpensive, synthetic, and rugged recognition element that can replace fragile antibodies, nucleic acids, enzymes, and other bioreceptors.

The highest specificity of binding between a biomolecule and a surface is currently achieved using affinity interaction between, for example, antibodies and antigen, receptor and ligand, etc. Both binding strength and specificity are important in specific binding reactions. Affinity-based systems often involve association constants in the range of $10^5$ to $10^9$ $M^{-1}$. Exploiting naturally occurring biological binding systems currently produces surfaces capable of specific, high-affinity binding with a preselected macromolecule. These systems recognize their target molecule by exploiting a combination of specific electrostatic interactions, hydrophobic interactions, hydrogen bonding, and shape.

Molecularly imprinted polymers (MIPs) have only recently been recognized as rugged, artificial recognition elements. MIPs have been prepared for a variety of small molecules with the affinity and specificity of the MIP for the target molecule approaching that observed for monoclonal antibodies. However, the preparation of MIPs for proteins and other large biomolecules have had limited success.

Mosbach and coworkers, as exemplified by U.S. Pat. Nos. 5,110,833 and 5,461,175, have developed what they call "molecular imprinting", which is a method of preparing polymers by polymerizing monomers around "print molecules". Molecular imprinting of synthetic polymers is a process where functional and cross-linking monomers are copolymerized in the presence of the target analyte, which acts as a molecular template. Before polymerization, the functional monomers either form a complex with the template via non-covalent interactions, or are covalently coupled forming a polymerizable derivative of the template. After polymerization, the functional groups of the monomers are held in position by the highly cross-linked polymeric structure. Subsequent removal of the template by solvent extraction or chemical cleavage reveals binding sites that are complementary in size and shape to the analyte. In this way, a molecular memory is introduced in the polymer, which is now capable of rebinding the analyte with very high specificity.

Originally, MIPs were employed as stationary phases in HPLC, notably for chiral separation. Subsequently, their use has been extended to other analytical techniques such as thin layer chromatography, capillary electrochromatography, solid-phase extraction, and immunoassay type binding assays. The binding sites often have affinities and selectivities approaching those of antibody-antigen systems, and have been dubbed antibody-binding mimics. These mimics display some clear advantages over real antibodies for sensor technology. Because of their highly cross-linked nature, MIPs are intrinsically stable and robust, facilitating their application in extreme environments, such as in the presence of acids, bases, or metal ions, in organic solvents, or at high temperatures and pressures. Moreover, MIPs are cheap to produce and can be stored in a dry state at room temperature for long periods of time. It is, therefore, not surprising that there is progress towards the use of MIPs as recognition elements in biomimetic sensors, large-scale separations (i.e. preparative chromatography or cleanup), and in the area of analytical chemistry for small-scale separations.

To the present date, imprinted polymer technology has had limited success for large molecular weight proteins and biomolecules, such as proteins, nucleic acids, and carbohydrates. The native state of a protein is usually a single, folded, globular structure where the hydrophobic amino acid side chains are buried in the interior of the protein and sequestered from bulk water. The denatured state of a protein is comprised of many random, unfolded structures where the hydrophobic amino acid side chains are exposed to bulk water. Although many other forces contribute to the stability of proteins, the hydrophobic effect is perhaps the main contributor to protein stability. Hydrophobic groups tend to organize the water molecules about them in hydrogen-bond cages called clathrates. The water molecules in clathrates are more ordered than the water molecules in bulk water. The entropic penalty of ordered water around hydrophobic groups in the denatured state drives the protein to the folded state. This effect is so great that it overcomes the concomitant decrease in entropy associated with folding the protein from an unfolded, denatured state to an ordered, native state. The driving force associated with removing hydrophobic side chains from bulk water is minimized or even absent when proteins are exposed to organic solvents. Consequently, in the presence of organic solvents, the entropy gain associated with unfolding the native state dominates and the protein unfolds. Despite this fact, the present methods of molecularly imprinting polymers involves dissolving the print molecule and monomer(s) in an organic solvent, and polymerization is initiated to ultimately yield the imprinted polymer.

Since proteins are most likely unfolded in the presence of organic solvents, the imprint formed during the polymerization of the monomers will be toward a non-native state of the target protein. Therefore, the interactions between print molecule and monomers during the polymerization in organic solvent would be considerably different than the interactions between the protein and MIP in water. The low dielectric medium of the organic solvent will screen hydrophobic interactions and exaggerate electrostatic interactions between the print molecule and monomers during polymerization. However, binding experiments are typically performed in water, which is a high dielectric medium, where electrostatic interactions will be screened while hydrophobic interactions will be exacerbated.

Attempts have been made to overcome the problems associated with imprinting proteins by avoiding the use of organic solvents in the imprinting process. Paliwal, et al., as exemplified in U.S. Pat. No. 5,756,717, describes the preparation of imprinted gels for use as a chromatographic separation media. The imprinted gels are made of agarose, which is a water insoluble, commercially available polysaccharide. The agarose is derivatized to prepare both positively and negatively charged agarose. The polymers are then heated to solubilize the agarose and then cooled to produce a gel. To prepare the imprint, the gel is heated to approximately 45° C. to melt the gel. Print molecule is added to the melted gel solution and the solution is cooled to generate the imprinted gel. The last step is the removal of the print molecule from the gel by washing the gel with a concentrated sodium chloride solution. This solution causes the print molecule to lose its affinity for the gel by screening the electrostatic interaction between the print molecule and the gel. This is a common method to remove bound biomolecules from ion exchange and affinity chromatography columns.

This technology has some serious limitations. The imaged agarose particles have limited thermal stability since they will melt near 45° C. and presumably loose their imprint. In addition, proteins with low thermal stability cannot be imprinted by this technique since they may unfold or denature at the temperature necessary to prepare the imprint. It should also be noted that this technique forms the imprint with prepolymerized compounds. Unlike Mosbach's methods in which the imprint is formed by polymerization, this technique simply reorients prepolymerized polymers into a new configuration to prepare the imprint.

A challenge associated with imprinting proteins and other biomolecules is the minimization of non-specific interactions between the protein to be bound and regions of the imprinted polymer that do not contain imprinted binding sites. Hjerten et al., as exemplified in U.S. Pat. No. 5,814,223, asserts that the presence of ionizable or charged groups in the imprinted polymer encourages non-specific binding and therefore, adversely affects specificity. They describe the preparation of imprinted polymers prepared with non-ionizing monomers (acrylamides, substituted acrylamides, and substituted methacrylates). Since ionizable side chains are intentionally avoided in the preparation of their imprinted polymers, the basis for the specific interaction between the target biomolecule and the imprinted polymer is adsorption into sites of the appropriate size and shape.

The limitation of this technology is that the recovery of bound (i.e. recognized) protein from the imprinted polymer is difficult. In Example 3 of U.S. Pat. No. 5,814,223, the recovery of hemoglobin from the hemoglobin specific column requires the use of a strongly denaturing solution. Therefore, the hemoglobin eluted from the column is likely irreversibly destroyed. These inventors suggest that desorption can be achieved by proteases degrading the adsorbed protein. Therefore, the applicability of this technology for isolation and purification of proteins is limited if powerful denaturants are required to elute the proteins from the imprinted polymers.

Therefore, there remains a need for a composition and method for preparing imprints of large molecular weight biomolecules in their native state. It would be desirable if the composition was easily prepared at room temperatures, stable at elevated temperatures, and allowed bound biomolecules to be eluted without denaturing.

SUMMARY OF THE INVENTION

The present invention provides a process for imprinting large molecular weight compounds like biomolecules into polymeric composite materials so that the imprinted materials are capable of specifically recognizing the print molecules once the print molecules are removed from the composite materials. The molecular imprinting process comprises:

a) dissolving a print molecule and a monomer in a first phase and dissolving a host polymer in a second phase, wherein the first and second phases are different phases selected from an aqueous phase and an organic phase;

b) preparing an emulsion of the aqueous phase and the organic phase;

c) polymerizing the monomer and forming a polymer composite at the interface in the emulsion;

d) separating the polymer composite from the emulsion using a solvent; and e) removing the print molecule from the composite using a solvent.

The present invention also provides a composite polymer that comprises one or more host polymers, such as polyalkylmethylacrylate, to enhance desired mechanical properties of the composite and one or more monomers that are polymerized in the presence of a print molecule and the host polymer to generate the imprinted polymer composite.

BRIEF DESCRIPTION OF THE DRAWINGS

So that the above recited features and advantages of the present invention can be understood in detail, a more particular description of the invention, briefly summarized above, may be had by reference to the embodiments thereof which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION OF THE INVENTION

The present invention provides a method for molecular imprinting polymers with large biomolecules. The imprinted composite is made by the interfacial polymerization of a monomer in the presence of the print molecule and host polymer. Since polymerization occurs at the interface between an organic solvent and an aqueous solution, the print molecule can be disposed in the phase that allows the print molecule to remain in its native configuration. The choice of a host polymer and a monomer to be polymerized can be varied to enhance the specificity of the composite toward the biomolecule that is selected to be imprinted.

The interfacial polymerization process involves an organic liquid phase and an aqueous liquid phase, in which are dissolved three components, the host polymer, monomers to be polymerized, and the compound to be imprinted (the print molecule). In Example 1 below, and similarly conceptually illustrated in FIG. 6, the host polymer is disposed in the organic phase and the monomer and print molecule are disposed in the aqueous phase. This distribution is not required. In fact, some biomolecules may loose their three dimensional structure when dissolved in aqueous solutions, for example lipids, glycolipids, and membrane proteins. Therefore, when imprinting some biomolecules it may be more appropriate to dissolve the print molecule and the monomer into the organic phase and a host polymer into the aqueous phase to yield the most specific imprinted composite. The most preferred phase for the host polymer, monomers to be polymerized, and the print molecule should be considered on a case-by-case basis, but the scope of the present invention anticipates molecularly imprinting polymers through interfacial polymerization processes having the print molecule and the monomer in the same phase and the host polymer in a different phase.

Figure 6:
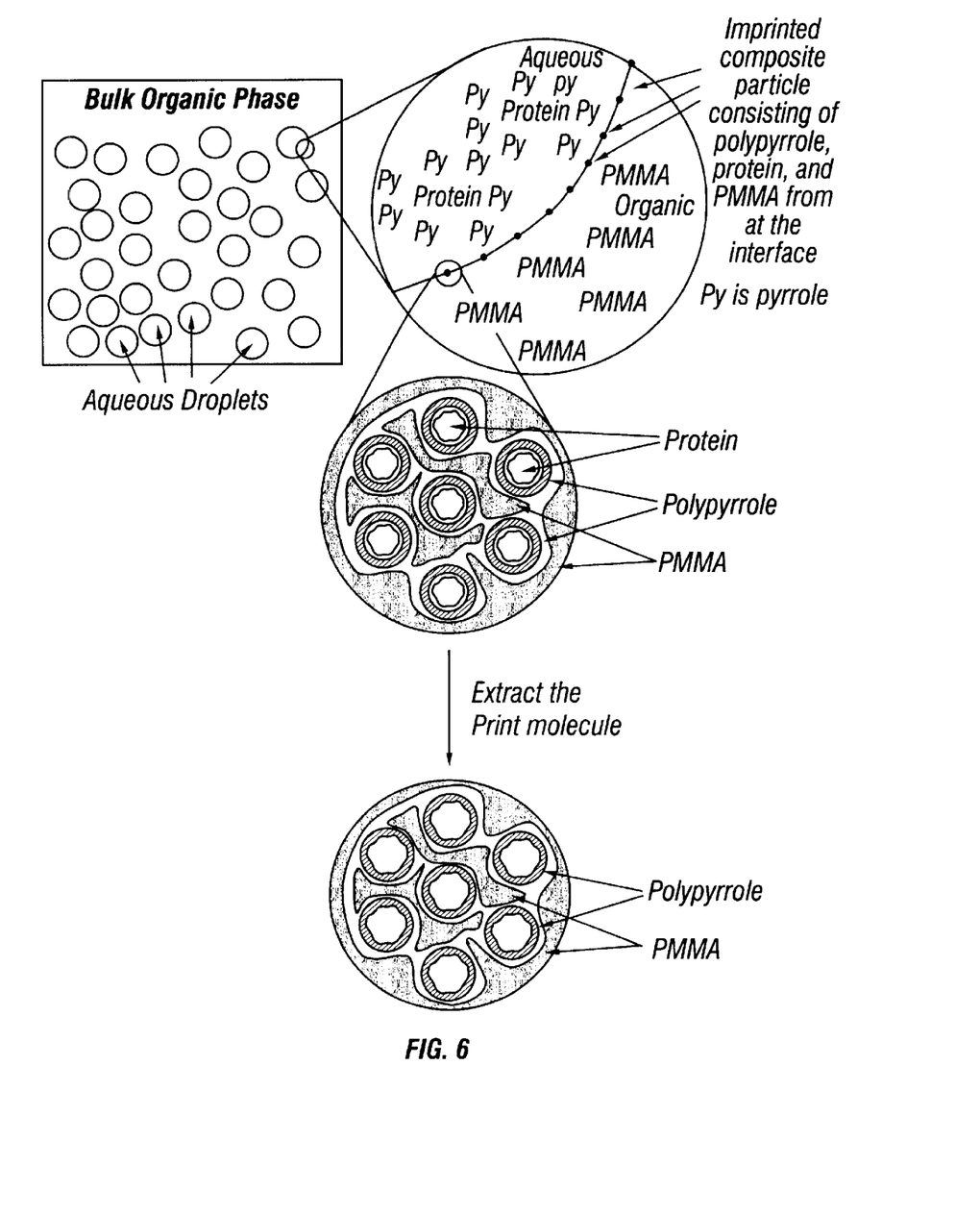
FIG. 6 is a conceptual diagram of the interfacial polymerization process and the resulting molecularly imprinted composite.

FIG. 6 is a conceptual diagram of the interfacial polymerization process used to prepare imprinted polymers. The host polymer (such as PMMA) is soluble in the organic phase (such as chloroform) while the molecule to be imprinted (such as HRP) and the monomer (such as pyrrole) are soluble in the aqueous phase. The monomer forms specific and non-specific interactions with the print molecule will form the basis of the specific binding site in the final product. Polymerization of the monomers begins through the addition of an initiator (such as ferric chloride). Although the monomer is soluble in the aqueous phase, the host polymer is not. Therefore, as the polymer extends in length, it accumulates at the interface between phases as it partitions from the aqueous phase and to the organic phase. The print molecule also accumulates at the interface through its interaction with the polymer. The resulting polymer and print molecule are trapped in this configuration by the host polymer in the organic phase. The result is composite particles consisting of host polymer, newly formed polymer, and print molecule. The composite particles are recovered and the print molecule extracted to yield composite particles with binding sites that are specific for the print molecule.

The imprinted polymer composite of the present invention preferably comprises an electronically conducting polymer. Electronically conductive polymers have interesting and useful electronic, optical, and redox properties and some of these polymers are environmentally stable. Electronically conducting polymer composites may be formed according to the foregoing method by selecting monomers that form conducting polymers, such monomers including, but not limited to, pyrrole, aniline, thiophene, and combinations thereof. The most preferred monomer being pyrrole.

Examples of imprintable molecules or print molecules include: proteins, enzymes, antibodies, antigens, hormones, peptides, polynucleotides, polynucleic acids (DNA, RNA), polypeptides, steroids, polyfatty acids, polyglucotides, polyglycerides, lipids, polysaccharides, whole cells, (both prokaryotic as well as eukaryotic), pathogens, spores, viruses, triglycerides, nucleotides, nucleic acid bases and their conjugates (ATP, ADP, AMP), and byproducts of biosynthesis of biomolecules.

The host polymer is believed to provide two main characteristics to the imprinted polymer composite: structural support and a source of functional groups to contribute to print molecule recognition. In Example 1 below, polymethylmethacrylate (PMMA) is the host polymer used to prepare an HRP specific polymer. The structure of PMMA is shown in FIG. 5 along with some related polymers. The host polymers are preferably selected from, but are not limited to, the varieties described in FIG. 5 and polyacrylic acid, polyacrylamide, polymethacrylamide, polyethacrylamide, polyalkacrylamides in general where the alkyl group is an aliphatic or aromatic group. Host polymers can also include polyamides, polyacrylonitrile, polybutadiene, polycaprolactone, polyethylene, polypropylene, polystyrene, polydivinylbenzene, polyethylene glycol, polypropylene glycol, polydimethylsiloxane, polylactide, polyglycolide, polyornithine, polyvinyl acetate, polyvinyl alcohol, polyvinyl chloride, polyvinyl isobutyl ether, polyvinyl methyl ether, polyurethane, and polyvinylpyrrolidone. Of particular utility are the poly amino acids such as polyalanine, polyvaline, polyleucine, polyisoleucine, polyglycine, polycysteine, polymethionine, polythreonine, polyserine, polylysine, polyarginine, polyhistidine, polyaspartic acid, polyglutamic acid, polyasparagine, polyglutamine, polytyrosine, polyphenylalanine, polytryptophan, and polyproline. Polysaccharides can also be used as a host polymer. These include chitin, chitosan, polydextrins, starch, agarose, and, cellulose. It is also envisioned that a mixture of polymers, copolymers, and/or block copolymers would also provide innovative ways to introduce the necessary functional groups to prepare a high-affinity, highly specific imprinted composite. In addition, use of biocompatible polymers, like polylactones, polyesters, polylactic acid, polygalactic acids or their copolymers can be used for biomedical applications.

The one or more monomers to be polymerized in the presence of the print molecule is important because it is a source of functional groups that provide specific and non-specific interactions with the print molecule. These interactions form the basis of the specific binding site in the resulting composite. Unlike the functional groups present in the host polymer, functional groups on the monomer have greater freedom to align into the proper orientation with the print molecule. Therefore, it is probably that these groups will contribute more to print molecule recognition than functional groups in the host polymer. Suitable monomers used in this invention include substituted or nonsubstituted acrylic acid, acrylonitriles, acrylamide, methacrylamide, ethacrylamide, alkacrylamides, and alkyl substituted alkyl acrylates in general where the alkyl group is an aliphatic or aromatic group. Monomers can also include acrylonitrile, butadiene, caprolactone, ethylene, propylene, styrene, divinylbenzene, ethylene glycol, propylene glycol, dimethylsiloxane, lactide, glycolide, ornithine, vinyl acetate, vinyl alcohol, vinyl chloride, vinyl isobutyl ether, vinyl methyl ether, urethane, isocyanates, isothiocyanates, and vinylpyrrolidone. Of particular utility are amino acids such as alanine, valine, leucine, isoleucine, glycine, cysteine, methionine, threonine, serine, lysine, arginine, histidine, aspartic acid, glutamic acid, asparagine, glutamine, tyrosine, phenylalanine, tryptophan, and proline. A mixture of monomers would also introduce the necessary functional groups to prepare a high-affinity, highly specific imprinted composite.

In addition, a variety of other compounds can be used before, during, or after the imprinting process to impart desired physical or chemical properties to the imprinted composite. If the composite is to be incorporated into an electronically conducting polymer sensor element, dopants can be added to improve the conductivity of the polymer composite. Similarly, fluorophores can be added that covalently or non-covalently incorporate into the polymer composite. Binding of the print molecule would quench the fluorophore and decrease the intensity of the fluorescence emission.

Producing the desired physical properties in the composite is also desirable and can be accomplished through additives. Plasticisers can be included to impart flexibility to the material. Other chemical additives capable of improving interfacial contacts can be added. Some examples include phase transfer catalysts like quaternaryammonium salts, other surfactants, dispersants and the like can be added to improve the physical or chemical properties of the composite.

In addition, variations of the pH in the imprinting process can bias the specificity towards certain ionizable groups. For example, preparing an imprint at low pH (acidic conditions) would protonate carboxyl groups in the system. This would minimize their contribution to specific electrostatic interactions involved in molecular recognition.

The choice of a solvent plays an important role in determining the porosity of the composite. Other organic solvents like dichloromethane, carbontetrachloride, or other halogenated solvents that are immiscible with water, such as toluene, benzene, ethyl acetate, ethers and the like, can be used as an organic phase.

There are three main methods used to polymerize pyrrole monomers: chemical, photochemical, and electrochemical polymerization. Chemical polymerization of pyrrole can be carried out using oxidative transition metal ions as an initiator, such as $FeCl_3$, $Fe(NO_3)_3$, $Fe(ClO_4)_3$, $Fe_2(SO_4)_3$, $CuCl_2$, $CuBr_2$, etc. Other methods to initiate and propagate polymerization, such as heating or irradiating (photochemical polymerization) the monomer solution with ultraviolet light, can also be used depending upon the chemical nature of the monomer to be polymerized. Therefore, depending upon the chemical nature of the monomer, polymerization of a monomer may be initiated and propagated by methods selected from photochemical, thermal, electrochemical, chemical or a combination thereof. Following polymerization, the composite polymer must be washed to remove the biomolecule.

The molecularly imprinted polymers of the present invention can be used to prepare separation media for specific biomolecules. An example would be the preparation of molecularly imprinted particles for the isolation and purification of recombinant proteins. These proteins are typically expressed in either bacteria or yeast and need to be: separated from other cellular proteins and biomolecules. The imprinted polymer composites can be packed into a column to form an affinity chromatography column. Cellular extracts containing the desired protein can be loaded onto the column and the molecular imprints or binding sites will preferentially bind the target protein to the exclusion of other cellular components. By washing with an appropriate solution (usually a buffer), residual cellular components are washed away from the column leaving only the desired protein immobilized on the imprinted polymer particles. The protein can then be eluted from the column by washing the column with a second buffer that has a different pH or ionic strength than the wash buffer. In example 1 below, HRP shows that the protein binds to the polymer at pH 7 but not pH 3.

Optionally, the composite MIPs can be formed on a variety of substrates, such as the surface of silica particles, polystyrene particles, or other chromatographic material to impart the necessary mechanical properties required in low- and high-pressure liquid chromatography. Particles with controlled pore sizes can be used as well. Composites can also be deposited on flat surfaces (glass, fiberglass, polymeric surfaces, natural surfaces, metal surfaces, electrodes, plastics) in the form of thin film. It may also be useful to form the imprinted polymer composites on the surface of magnetic particles that can be simply dumped into a solution containing the target biomolecule. Following a suitable incubation time necessary for binding of the target biomolecule to the imprinted particles, the magnetic particles can be collected with a magnet, washed with buffer, and the target biomolecule can be eluted from the particles. Alternatively, the imprinted polymer composites can also be cast as a membrane or coated onto existing membranes. The resulting separation membranes are highly specific for the target biomolecule.

In addition, the imprinted polymer composites can be used as sensor elements. The composites can be cast into films on a variety of surfaces and used to bind the target biomolecule. The polymer composite may be formed into a sensor selected from a membrane, coating, paint, beads, microspheres, or combinations thereof. The presence of the biomolecule on the imprinted surface can be determined by a variety of techniques including spectroscopy, electrochemistry, or microscopy. For example, a change in conductivity of an electronically conducting, imprinted polymer (polypyrrole) composite, such as a composite formed by polymerizing water-soluble pyrrole monomers, is detectable upon binding of the target biomolecule to the surface of the composite.

Other applications for the present MIPs include the preparation of artificial enzymes, separation of racemic mixtures, DNA recognition, and the preparation of water-soluble MIPs as artificial antibodies. The technology can be also used to prepare whole-cell and virus imprints. Similar to large biomolecules, whole cells and viruses will adopt a non-native conformation when placed in organic solvents. This technology will enable the native conformation of the cells and viruses to be imprinted.

EXAMPLE 1
Imprinting Horseradish Peroxidase in a Polymer Composite

A molecular imprinted polymer was prepared using polymethylmethacrylate (PMMA) as the host polymer, pyrrole (PPY) as the monomer, and Horseradish Peroxidase (HRP) as the print molecule. HRP was selected as the print molecule because it is a large protein (MW=44 kD) and also because it is an enzyme that can be easily quantified with a simple colorimetric assay.

The HRP imprinted composite was prepared using an interfacial (emulsion) polymerization technique. First, 0.8 g. of PMMA was dissolved in 10 mL of chloroform. A separate 2 mL solution containing 0.2 g sodium dodecylsulfate (SDS) surfactant, 0.1 g of pyrrole and 25 mg HRP in water was also prepared. The two solutions were mixed with vigorous stirring to form an emulsion. 10 ml of an aqueous solution containing 0.5 g ferric chloride was introduced dropwise to the emulsion with stirring to polymerize the pyrrole. The polymerization reaction was allowed to continue for 3 hours with stirring. The PMMA/PPY composite was precipitated upon the addition of 25 mL of methanol, with stirring. The entire process was done at room temperature. The precipitate was filtered, washed with methanol and water several times, and finally dried at 40° C. in vacuum for 24 hours. This process produced 0.86 g of the PMMA/PPY composite or a 96% yield. Blank or non-imprinted polymer was prepared in the same manner except HRP was omitted from the aqueous solution.

Figure 1:
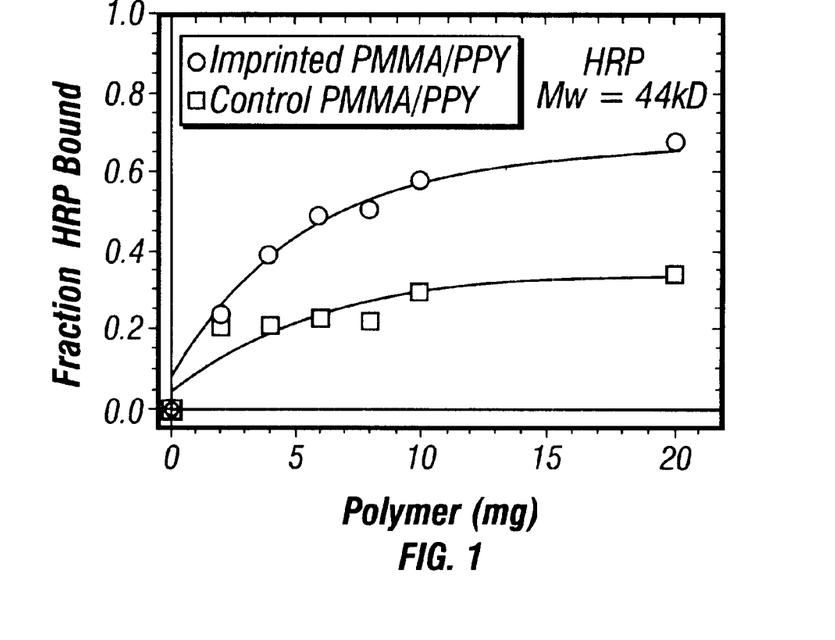
FIG. 1 is a graph of the fraction of HRP bound to an imprinted polymethylmethacrylate/polypyrrole composite and a control polymethylmethacrylate/polypyrrole composite.

The capability of the HRP imprinted PMMA/PPY composite to bind HRP was compared to the control PMMA/PPY composite. This was measured by incubating HRP with polymer and determining the amount of HRP in solution after a predetermined length of time. Specifically, 0.5 mL of 0.08 µg/mL HRP was added to a 0.7 mL eppendorf tube that contained from 0 to 20 mg of either imprinted or control PMMA/PPY composite. The HRP solution was provided at pH 7 and also contained a 10-fold molar excess of Bovine Serum Albumin (BSA) to crudely simulate a complex mixture. The eppendorfs were gently agitated. After 30 minutes, the polymer was allowed to settle to the bottom of the tubes and a 10 µL aliquot from each of the tubes was transferred to wells in a microtliter plate. 200 µL of ABTS One-Step (a 1-Step TM ABTS 2,2'Azine-di[3-ethylbenzthiazoline sulfonate] available from Pierce Chemical Company of Rockford, Ill.) was added to all of the wells. The fraction of HRP bound, $f_b$, is simply unity minus the fraction of HRP in solution, $f_s$. $f_s$ is defined as the absorbance at 405 nm of any sample divided by the absorbance of a control sample that contained no polymer (i.e. a solution in which 100% of the HRP was in solution). The results from this experiment, shown in FIG. 1, make it apparent that HRP binds better to the imprinted PMMA/PPY composite than to the control PMMA/PPY composite. However, a considerable amount of HRP still bound to the control polymer.

EXAMPLE 2
The Imprinted Polymer Composite Recognizes the Size of HRP

Figure 2:
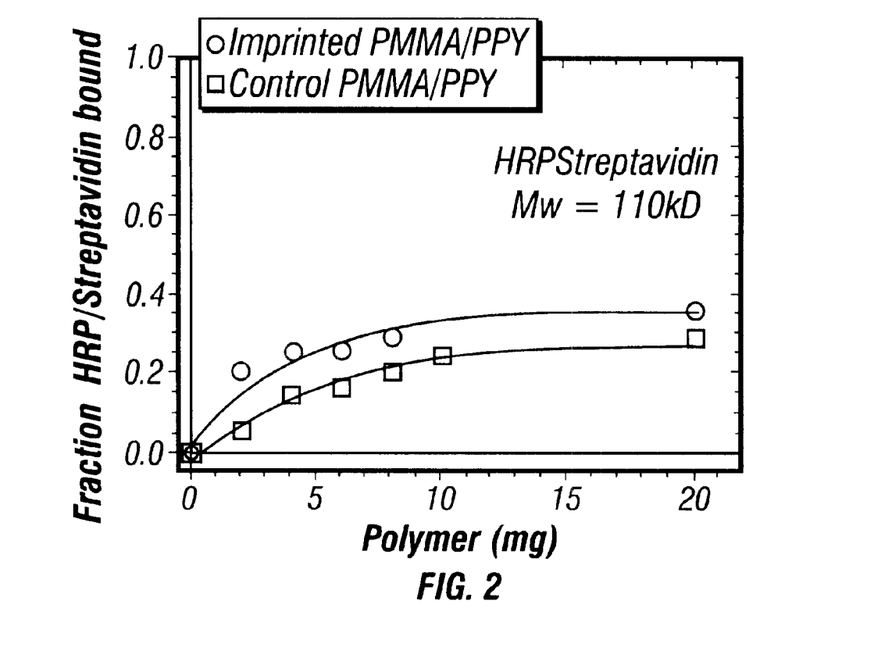
FIG. 2 is a graph of the fraction of HRP/Streptavidin bound to an imprinted polymethylmethacrylate/polypyrrole composite and a control polymethylmethacrylate/polypyrrole composite.

FIG. 2 shows another experiment performed to determine the nature of the HRP interaction with the imprinted PMMA/PPY composite. Instead of HRP, a solution containing HRP/Streptavidin was prepared and incubated with control and HRP imprinted polymer. HRP/Streptavidin is a covalently coupled heterodimer between one HRP molecule and one Streptavidin molecule. It is apparent from FIG. 2 that HRP/Streptavidin does not bind as well as HRP to the imprinted composite. In fact, the binding of HRP/Streptavidin is similar to that of HRP to control polymer suggesting that the interaction between HRP/Streptavidin and imprinted composite are non-specific. Since the molecular weight of the HRP/Streptavidin heterodimer is approximately 110 kD, it is presumed that the binding of HRP to the imprinted copolymer is strongly size dependent. Presumably, HRP can penetrate the polymer particles and bind while the large HRP/Streptavidin cannot.

Figure 3:
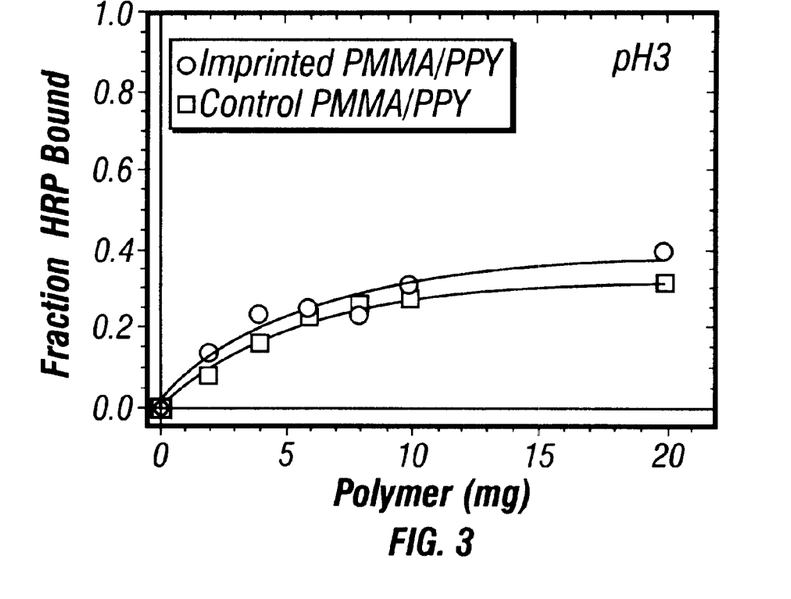
FIG. 3 is a graph of the fraction of HRP bound to an imprinted polymethylmethacrylate/polypyrrole composite and a control poltymethylmethacrylate/polypyrrole composite at a pH of 3.

EXAMPLE 3
The Imprinted Polymer Composite Recognizes Ionizable Groups on the Surface of HRP Another experiment was performed to further understand the nature of the interaction between HRP and the imprinted polymer. The binding of HRP to each imprinted polymer was determined at pH 3 and compared to the previously determined binding at pH 7. From the results of the experiment at pH 3, shown in FIG. 3, it is apparent that the binding of HRP to the imprinted polymer is pH dependent. HRP binds to the imprinted polymer, better at pH 7 than it does at pH 3. It is also important to note that the binding of HRP to the control polymer is the same at pH 7 and pH 3. Measuring binding as a function of pH reveals the contribution of ionizable groups to the interaction between HRP and the polymer. A change in pH from 7 to 3 results, primarily, in the protonation of carboxyl groups on HRP. This suggests that ionized carboxyl groups in HRP participate in the interaction between HRP and the imprinted PMMA/PPY composite. Also there is a possibility of partial protonation of the pyrrole nitrogen at lower pH values that will effect binding of protein in the imprint cavity. (Pka of secondary amine is between 10–11). In addition, since the dependence of binding on pH is not observed with the control polymer, the interactions between HRP and the imprinted polymer must be specific (i.e. a genuine HRP imprint has been formed in the imprinted polymer).

EXAMPLE 4
Biomolecule Sensors

Figure 4:
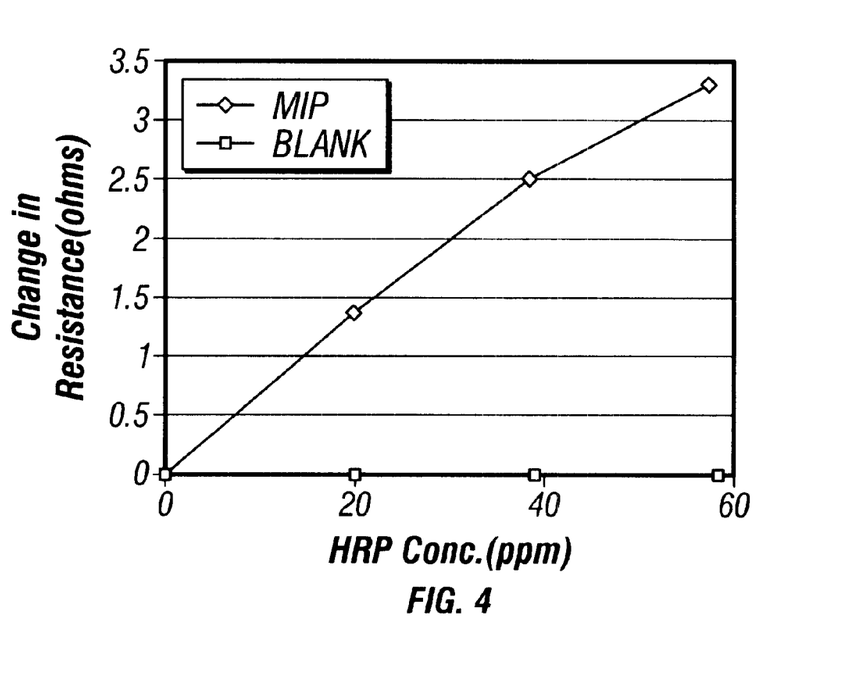
FIG. 4 is a graph of the change in electronic resistance of the composite as a function of the HRP concentration in the solution.
Figure 5A:
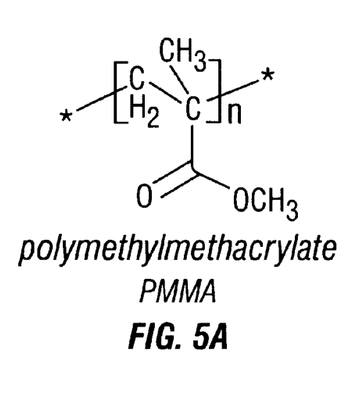
FIG. 5 is a chart showing the structures of various host polymers.
Figure 5B:
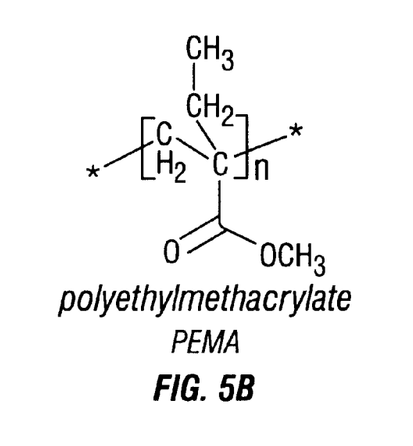
Figure 5C:
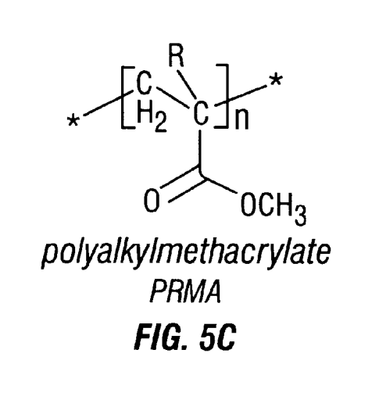
Figure 5D:
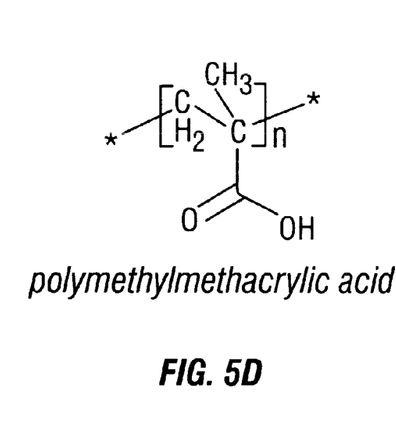
Figure 5E:
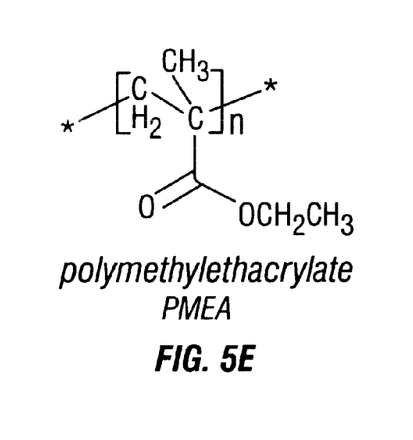
Figure 5F:
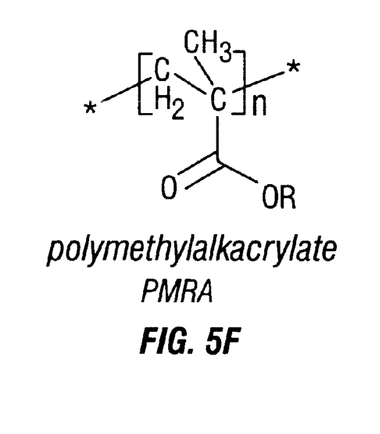

Experiments were performed to understand the application of the imprinted polymer composite for development of sensors that will selectively detect a print molecule from a solution. In order to get the desired level of electrical conductivity in the composite, different ratios of print molecule to monomer were tried. First, 0.8 g of PMMA was dissolved in 10 mL of chloroform to form an organic solution. A separate solution containing 0.2 g sodium dodecylsulfate (SDS) surfactant, 0.5 g of pyrrole, and 50 mg HRP in 2 mL water was also prepared to form an aqueous solution. The two solutions were mixed with vigorous stirring to form an emulsion. 10 ml of an aqueous solution containing 01.0 g ferric chloride was introduced dropwise to the emulsion with stirring to polymerize the pyrrole. The polymerization reaction was allowed to continue for 3 hours with stirring. The PMMA/PPY composite was precipitated upon the addition of 25 mL of methanol, with stirring. The entire process was done at room temperature. The precipitate was filtered, washed with methanol and water several times, and finally dried at 40° C. in a vacuum for 24 hours. This process produced 1.26 g of the PMMA/PPY composite. Blank or non-imprinted polymer was prepared in the same manner except HRP was omitted. from the aqueous solution. The resulting polymer was pressed in to a palette (1 cm radius) at 5000 psi pressure using a manual hydrolytic press at room temperature. The discs were found to be electronically conducting with resistance in the range of 1.0 ohms to 1.0 k.ohms. These discs were conditioned in phosphate buffer (0.1 millimolar, pH 7.0) for 48 hours before conductivity experiments were conducted. The results of these experiments are presented in FIG. 4.

The term "comprising" means that the recited elements or steps may be only part of the device and does not exclude additional unrecited elements or steps.

It will be understood that certain combinations and subcombinations of the invention are of utility and may be employed without reference to other features in subcombinations. This is contemplated by and is within the scope of the present invention. As many possible embodiments may be made of this invention without departing from the spirit and scope thereof, it is to be understood that all matters hereinabove set forth or shown in the accompanying drawings are to be interpreted as illustrative and not in a limiting sense.

What is claimed is:

1. A method of preparing a molecularly imprinted polymer, the method comprising:
   (a) dissolving a print molecule and a monomer in a first phase and dissolving a host polymer in a second phase, wherein the first and second phases are different phases and selected from an aqueous phase and an organic phase;

(b) preparing an emulsion of the aqueous phase and the organic phase;

(c) polymerizing the monomer to form a polymer composite with the host polymer along an interface between the first and second phases;

(d) separating the polymer composite from the emulsion; and removing the print molecule from the composite.

2. The method of claim 1, wherein the first phase is an aqueous phase.

3. The method of claim 2, wherein the print molecule is selected from the group consisting of proteins, enzymes, antibodies, antigens, hormones, peptides, polynucleotides, polynucleic acids, polypeptides, steroids, polyfatty acids, polyglucotides, polyglycerides, lipids, polysaccharides, whole cells, pathogens, viruses, triglycerides, nucleotides, nucleic acid bases and their conjugates, byproducts of biosynthesis of biomolecules, and combinations thereof.

4. The method of claim 2, wherein the host polymer is selected from the group polymethylmethacrylate, polyacrylic acid, polyacrylamide, polymethacrylamide, polyethacrylamide, polyalkacrylamides, polyamides, polyacrylonitrile, polybutadiene, polycaprolactone, polyethylene, polypropylene, polystyrene, polydivinylbenzene, polyethylene glycol, polypropylene glycol, polydimethylsiloxane, polylactide, polyglycolide, polyornithine, polyvinyl acetate, polyvinyl alcohol, polyvinyl chloride, polyvinyl isobutyl ether, polyvinyl methyl ether, polyurethane, and polyvinylpyrrolidone.

5. The method of claim 2, wherein the host polymer is a poly amino acids selected from the group consisting of polyalanine, polyvaline, polyleucine, polyisoleucine, polyglycine, polycysteine, polymethionine, polythreonine, polyserine, polylysine, polyarginine, polyhistidine, polyaspartic acid, polyglutamic acid, polyasparagine, polyglutamine, polytyrosine, polyphenylalanine, polytryptophan, polyproline, and combinations thereof.

6. The method of claim 2, wherein the host polymer is a polysaccharide or a polycarbohydrate.

7. The method of claim 2, wherein the host polymer is selected from the group consisting of chitin, chitosan, polydextrins, starch, agarose, cellulose and combinations thereof.

8. The method of claim 2, wherein the host polymer is selected from the group consisting of a copolymer, a block copolymer, and mixtures thereof.

9. The method of claim 2, wherein the host polymer is a biocompatible polymer selected from the group consisting of polylactones, polyesters, polylactic acid, polygalactic acids, and combinations or copolymers thereof.

10. The method of claim 2, wherein the monomers produce electronically conducting polymers.

11. The method of claim 10, wherein the electronic conductivity of the imprinted polymer changes when print molecules bind to imprints in the polymer composite.

12. The method of claim 2, wherein the monomers are selected from the group consisting of pyrrole, aniline, thiophene, and combinations thereof.

13. The method of claim 2, wherein the monomers are selected from the group consisting of substituted or nonsubstituted acrylic acid, acrylonitriles, acrylamide, methacrylamide, ethacrylamide, alkacrylamides, alkyl substituted alkyl acrylates, acrylonitrile, butadiene, caprolactone, ethylene, propylene, styrene, divinylbenzene, ethylene glycol, propylene glycol, dimethylsiloxane, lactide, glycolide, ornithine, vinyl acetate, vinyl alcohol, vinyl chloride, vinyl isobutyl ether, vinyl methyl ether, urethane, isocyanates, isothiocyanates, vinylpyrrolidone, and combinations thereof.

14. The method of claim 2, wherein the monomers are amino acids selected from the group consisting of alanine, valine, leucine, isoleucine, glycine, cysteine, methionine, threonine, serine, lysine, arginine, histidine, aspartic acid, glutamic acid, asparagine, glutamine, tyrosine, phenylalanine, tryptophan, proline, and combinations thereof.

15. The method of claim 2, wherein the monomer comprises a mixture of monomers having different functional groups.

16. The method of claim 2, wherein the first and second phases further comprise one or more additives selected from the group consisting of dopants to improve the conductivity of the polymer, fluorophores, plasticisers, phase transfer catalysts, surfactants, dispersants, and combinations thereof.

17. The method of claim 2, wherein the pH is between about 6 and about 8.

18. The method of claim 2, wherein the polymerization is selected from the group consisting of photochemical, thermal, electrochemical, chemical or a combination thereof.

19. The method of claim 2, wherein the step of polymerizing the monomer comprises adding an aqueous solution of an electron acceptor into the emulsion.

20. The method of claim 19, wherein the step of initiating polymerization of the monomer comprises adding an aqueous solution of an initiator selected from the group consisting of $FeCl_3$, $Fe(NO_3)_3$, $Fe(ClO_4)_3$, $Fe_2(SO4)_3$, $CuCl_2$, and $CuBr_2$.

21. The method of claim 2, further comprising:
(f) precipitating the polymer composite out of the emulsion.

22. The method of claim 2, wherein the first phase maintains the print molecule in its native configuration.

23. The method of claim 2, further comprising:
(f) forming the polymer composite into a sensor selected from a membrane, coating, paint, beads, microspheres, or combinations thereof.

24. The method of claim 23, wherein the step of forming the polymer composite includes a process selected from the group consisting of casting a layer and compressing into a disc.

25. The molecularly imprinted polymer formed by the method of claim 2.

26. The method of claim 2, wherein the step of separating the polymer composite from the emulsion further comprises using a first solvent and wherein the step of removing the print molecule from the composite further comprises using a second solvent.

27. The method of claim 26, wherein the print molecule is selected from the group consisting of proteins, enzymes, antibodies, antigens, hormones, peptides, polynucleotides, polynucleic acids, polypeptides, steroids, polyfatty acids, polyglucotides, polyglycerides, lipids, polysaccharides, whole cells, pathogens, viruses, triglycerides, nucleotides, nucleic acid bases and their conjugates, byproducts of biosynthesis of biomolecules, and combinations thereof.

28. The method of claim 26, wherein the host polymer is selected from the group polymethylmethacrylate, polyacrylic acid, polyacrylamide, polymethacrylamide, polyethacrylamide, polyalkacrylamides, polyamides, polyacrylonitrile, polybutadiene, polycaprolactone, polyethylene, polypropylene, polystyrene, polydivinylbenzene, polyethylene glycol, polypropylene glycol, polydimethylsiloxane, polylactide, polyglycolide, polyornithine, polyvinyl acetate, polyvinyl alcohol, polyvinyl chloride, polyvinyl isobutyl ether, polyvinyl methyl ether, polyurethane, and polyvinylpyrrolidone.

29. The method of claim 26, wherein the host polymer is a poly amino acids selected from the group consisting of polyalanine, polyvaline, polyleucine, polyisoleucine, polyglycine, polycysteine, polymethionine, polythreonine, polyserine, polylysine, polyarginine, polyhistidine, polyaspartic acid, polyglutamic acid, polyasparagine, polyglutamine, polytyrosine, polyphenylalanine, polytryptophan, polyproline, and combinations thereof.

30. The method of claim 26, wherein the host polymer is a polysaccharide or a polycarbohydrate.

31. The method of claim 26, wherein the host polymer is selected from the group consisting of chitin, chitosan, polydextrins, starch, agarose, cellulose and combinations thereof.

32. The method of claim 26, wherein the host polymer is selected from the group consisting of a copolymer, a block copolymer, and mixtures thereof.

33. The method of claim 26, wherein the host polymer is a biocompatible polymer selected from the group consisting of polylactones, polyesters, polylactic acid, polygalactic acids, and combinations or copolymers thereof.

34. The method of claim 26, wherein the monomers produce electronically conducting polymers.

35. The method of claim 34, wherein the electronic conductivity of the imprinted polymer changes when print molecules bind to imprints in the polymer composite.

36. The method of claim 26, wherein the monomers are selected from the group consisting of pyrrole, aniline, thiophene, and combinations thereof.

37. The method of claim 26, wherein the monomers are selected from the group consisting of substituted or nonsubstituted acrylic acid, acrylonitriles, acrylamide, methacrylamide, ethacrylamide, alkacrylamides, alkyl substituted alkyl acrylates, acrylonitrile, butadiene, caprolactone, ethylene, propylene, styrene, divinylbenzene, ethylene glycol, propylene glycol, dimethylsiloxane, lactide, glycolide, ornithine, vinyl acetate, vinyl alcohol, vinyl chloride, vinyl isobutyl ether, vinyl methyl ether, urethane, isocyanates, isothiocyanates, vinylpyrrolidone, and combinations thereof.

38. The method of claim 26, wherein the monomers are amino acids selected from the group consisting of alanine, valine, leucine, isoleucine, glycine, cysteine, methionine, threonine, serine, lysine, arginine, histidine, aspartic acid, glutamic acid, asparagine, glutamine, tyrosine, phenylalanine, tryptophan, proline, and combinations thereof.

39. The method of claim 26, wherein the monomer comprises a mixture of monomers having different functional groups.

40. The method of claim 26, wherein the first and second phases further comprise one or more additives selected from the group consisting of dopants to improve the conductivity of the polymer, fluorophores, plasticisers, phase transfer catalysts, surfactants, dispersants, and combinations thereof.

41. The method of claim 26, wherein the pH is between about 6 and about 8.

42. The method of claim 26, wherein the polymerization is selected from the group consisting of photochemical, thermal, electrochemical, chemical or a combination thereof.

43. The method of claim 26, wherein the step of polymerizing the monomer comprises adding an aqueous solution of an electron acceptor into the emulsion.

44. The method of claim 43, wherein the step of initiating polymerization of the monomer comprises adding an aqueous solution of an initiator selected from the group consisting of $FeCl_3$, $Fe(NO_3)_3$, $Fe(ClO_4)_3$, $Fe_2(SO4)_3$, $CuCl_2$, and $CuBr_2$.

45. The method of claim 26, further comprising:
(f) precipitating the polymer composite out of the emulsion.

46. The method of claim 26, wherein the first phase maintains the print molecule in its native configuration.

47. The method of claim 26, further comprising:
(f) forming the polymer composite into a sensor selected from a membrane, coating, paint, beads, microspheres, or combinations thereof.

48. The method of claim 47, wherein the step of forming the polymer composite includes a process selected from the group consisting of casting a layer and compressing into a disc.

49. The molecularly imprinted polymer formed by the method of claim 26.

50. The method of claim 1, wherein the first phase is an organic phase.

51. The method of claim 50, wherein the print molecule is selected from the group consisting of proteins, enzymes, antibodies, antigens, hormones, peptides, polynucleotides, polynucleic acids, polypeptides, steroids, polyfatty acids, polyglucotides, polyglycerides, lipids, polysaccharides, whole cells, pathogens, viruses, triglycerides, nucleotides, nucleic acid bases and their conjugates, byproducts of biosynthesis of biomolecules, and combinations thereof.

52. The method of claim 50, wherein the host polymer is selected from the group polymethylmethacrylate, polyacrylic acid, polyacrylamide, polymethacrylamide, polyethacrylamide, polyalkacrylamides, polyamides, polyacrylonitrile, polybutadiene, polycaprolactone, polyethylene, polypropylene, polystyrene, polydivinylbenzene, polyethylene glycol, polypropylene glycol, polydimethylsiloxane, polylactide, polyglycolide, polyornithine, polyvinyl acetate, polyvinyl alcohol, polyvinyl chloride, polyvinyl isobutyl ether, polyvinyl methyl ether, polyurethane, and polyvinylpyrrolidone.

53. The method of claim 50, wherein the host polymer is a poly amino acids selected from the group consisting of polyalanine, polyvaline, polyleucine, polyisoleucine, polyglycine, polycysteine, polymethionine, polythreonine, polyserine, polylysine, polyarginine, polyhistidine, polyaspartic acid, polyglutamic acid, polyasparagine, polyglutamine, polytyrosine, polyphenylalanine, polytryptophan, polyproline, and combinations thereof.

54. The method of claim 50, wherein the host polymer is a polysaccharide or a polycarbohydrate.

55. The method of claim 50, wherein the host polymer is selected from the group consisting of chitin, chitosan, polydextrins, starch, agarose, cellulose and combinations thereof.

56. The method of claim 50, wherein the host polymer is selected from the group consisting of a copolymer, a block copolymer, and mixtures thereof.

57. The method of claim 50, wherein the host polymer is a biocompatible polymer selected from the group consisting of polylactones, polyesters, polylactic acid, polygalactic acids, and combinations or copolymers thereof.

58. The method of claim 50, wherein the monomers produce electronically conducting polymers.

59. The method of claim 58, wherein the electronic conductivity of the imprinted polymer changes when print molecules bind to imprints in the polymer composite.

60. The method of claim 50, wherein the monomers are selected from the group consisting of pyrrole, aniline, thiophene, and combinations thereof.

61. The method of claim 50, wherein the monomers are selected from the group consisting of substituted or nonsubstituted acrylic acid, acrylonitriles, acrylamide, methacrylamide, ethacrylamide, alkacrylamides, alkyl substituted alkyl acrylates, acrylonitrile, butadiene, caprolactone, ethylene, propylene, styrene, divinylbenzene, ethylene glycol, propylene glycol, dimethylsiloxane, lactide, glycolide, ornithine, vinyl acetate, vinyl alcohol, vinyl chloride, vinyl isobutyl ether, vinyl methyl ether, urethane, isocyanates, isothiocyanates, vinylpyrrolidone, and combinations thereof.

62. The method of claim 50, wherein the monomers are amino acids selected from the group consisting of alanine, valine, leucine, isoleucine, glycine, cysteine, methionine, threonine, serine, lysine, arginine, histidine, aspartic acid, glutamic acid, asparagine, glutamine, tyrosine, phenylalanine, tryptophan, proline, and combinations thereof.

63. The method of claim 50, wherein the monomer comprises a mixture of monomers having different functional groups.

64. The method of claim 50, wherein the first and second phases further comprise one or more additives selected from the group consisting of dopants to improve the conductivity of the polymer, fluorophores, plasticisers, phase transfer catalysts, surfactants, dispersants, and combinations thereof.

65. The method of claim 50, wherein the pH is between about 6 and about 8.

66. The method of claim 50, wherein the polymerization is selected from the group consisting of photochemical, thermal, electrochemical, chemical or a combination thereof.

67. The method of claim 50, wherein the step of polymerizing the monomer comprises adding an aqueous solution of an electron acceptor into the emulsion.

68. The method of claim 67, wherein the step of initiating polymerization of the monomer comprises adding an aqueous solution of an initiator selected from the group consisting of $FeCl_3$, $Fe(NO_3)_3$, $Fe(ClO_4)_3$, $Fe_2(SO4)_3$, $CuCl_2$, and $CuBr_2$.

69. The method of claim 50, further comprising:
(f) precipitating the polymer composite out of the emulsion.

70. The method of claim 50, wherein the first phase maintains the print molecule in its native configuration.

71. The method of claim 50, further comprising:
(f) forming the polymer composite into a sensor selected from a membrane, coating, paint, beads, microspheres, or combinations thereof.

72. The method of claim 71, wherein the step of forming the polymer composite includes a process selected from the group consisting of casting a layer and compressing into a disc.

73. The molecularly imprinted polymer formed by the method of claim 50.

74. The method of claim 50, wherein the step of separating the polymer composite from the emulsion further comprises using a first solvent and wherein the step of removing the print molecule from the composite further comprises using a second solvent.

75. The method of claim 50, wherein the print molecule is selected from the group consisting of proteins, enzymes, antibodies, antigens, hormones, peptides, polynucleotides, polynucleic acids, polypeptides, steroids, polyfatty acids, polyglucotides, polyglycerides, lipids, polysaccharides, whole cells, pathogens, viruses, triglycerides, nucleotides, nucleic acid bases and their conjugates, byproducts of biosynthesis of biomolecules, and combinations thereof.

76. The method of claim 74, wherein the host polymer is selected from the group consisting of polymethylmethacrylate, polyacrylic acid, polyacrylamide, polymethacrylamide, polyethacrylamide, polyalkacrylamides, polyamides, polyacrylonitrile, polybutadiene, polycaprolactone, polyethylene, polypropylene, polystyrene, polydivinylbenzene, polyethylene glycol, polypropylene glycol, polydimethylsiloxane, polylactide, polyglycolide, polyornithine, polyvinyl acetate, polyvinyl alcohol, polyvinyl chloride, polyvinyl isobutyl ether, polyvinyl methyl ether, polyurethane, and polyvinylpyrrolidone.

77. The method of claim 74, wherein the host polymer is a poly amino acids selected from the group consisting of polyalanine, polyvaline, polyleucine, polyisoleucine, polyglycine, polycysteine, polymethionine, polythreonine, polyserine, polylysine, polyarginine, polyhistidine, polyaspartic acid, polyglutamic acid, polyasparagine, polyglutamine, polytyrosine, polyphenylalanine, polytryptophan, polyproline, and combinations thereof.

78. The method of claim 74, wherein the host polymer is a polysaccharide or a polycarbohydrate.

79. The method of claim 74, wherein the host polymer is selected from the group consisting of chitin, chitosan, polydextrins, starch, agarose, cellulose and combinations thereof.

80. The method of claim 74, wherein the host polymer is selected from the group consisting of a copolymer, a block copolymer, and mixtures thereof.

81. The method of claim 74, wherein the host polymer is a biocompatible polymer selected from the group consisting of polylactones, polyesters, polylactic acid, polygalactic acids, and combinations or copolymers thereof.

82. The method of claim 74, wherein the monomers produce electronically conducting polymers.

83. The method of claim 82, wherein the electronic conductivity of the imprinted polymer changes when print molecules bind to imprints in the polymer composite.

84. The method of claim 74, wherein the monomers are selected from the group consisting of pyrrole, aniline, thiophene, and combinations thereof.

85. The method of claim 74, wherein the monomers are selected from the group consisting of substituted or nonsubstituted acrylic acid, acrylonitriles, acrylamide, methacrylamide, ethacrylamide, alkacrylamides, alkyl substituted alkyl acrylates, acrylonitrile, butadiene, caprolactone, ethylene, propylene, styrene, divinylbenzene, ethylene glycol, propylene glycol, dimethylsiloxane, lactide, glycolide, ornithine, vinyl acetate, vinyl alcohol, vinyl chloride, vinyl isobutyl ether, vinyl methyl ether, urethane, isocyanates, isothiocyanates, vinylpyrrolidone, and combinations thereof.

86. The method of claim 74, wherein the monomers are amino acids selected from the group consisting of alanine, valine, leucine, isoleucine, glycine, cysteine, methionine, threonine, serine, lysine, arginine, histidine, aspartic acid, glutamic acid, asparagine, glutamine, tyrosine, phenylalanine, tryptophan, proline, and combinations thereof.

87. The method of claim 74, wherein the monomer comprises a mixture of monomers having different functional groups.

88. The method of claim 74, wherein the first and second phases further comprise one or more additives selected from the group consisting of dopants to improve the conductivity of the polymer, fluorophores, plasticisers, phase transfer catalysts, surfactants, dispersants, and combinations thereof.

89. The method of claim 74, wherein the pH is between about 6 and about 8.

90. The method of claim 74, wherein the polymerization is selected from the group consisting of photochemical, thermal, electrochemical, chemical or a combination thereof.

91. The method of claim 74, wherein the step of polymerizing the monomer comprises adding an aqueous solution of an electron acceptor into the emulsion.

92. The method of claim 91, wherein the step of initiating polymerization of the monomer comprises adding an aqueous solution of an initiator selected from the group consisting of $FeCl_3$, $Fe(NO_3)_3$, $Fe(ClO_4)_3$, $Fe_2(SO4)_3$, $CuCl_2$, and $CuBr_2$.

93. The method of claim 74, further comprising:
(f) precipitating the polymer composite out of the emulsion.

94. The method of claim 74, wherein the first phase maintains the print molecule in its native configuration.

95. The method of claim 74, further comprising:
(f) forming the polymer composite into a sensor selected from a membrane, coating, paint, beads, microspheres, or combinations thereof.

96. The method of claim 95, wherein the step of forming the polymer composite includes a process selected from the group consisting of casting a layer and compressing into a disc.

97. The molecularly imprinted polymer formed by the method of claim 74.

* * * * *